US00PP31262P3

(12) United States Plant Patent
van Straaten et al.

(10) Patent No.: US PP31,262 P3
(45) Date of Patent: Dec. 24, 2019

(54) ***HYDRANGEA* PLANT NAMED 'STRARED'**

(50) Latin Name: *Hydrangea macrophylla*
Varietal Denomination: Strared

(71) Applicants: Jan van Straaten, Harderwijk (NL); Johan van Straaten, Harderwijk (NL)

(72) Inventors: Jan van Straaten, Harderwijk (NL); Johan van Straaten, Harderwijk (NL)

( * ) Notice: Subject to any disclaimer, the term of this patent is extended or adjusted under 35 U.S.C. 154(b) by 0 days.

(21) Appl. No.: 15/932,854

(22) Filed: May 8, 2018

(65) Prior Publication Data

US 2019/0350114 P1 Nov. 14, 2019

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — The Webb Law Firm

(57) ABSTRACT

A new and distinct *Hydrangea* plant having multicolored flowers and strong stems.

2 Drawing Sheets

Botanical classification: *Hydrangea macrophylla.*
Varietal denomination: 'Strared'.

BACKGROUND OF THE INVENTION

The present invention comprises a new and distinct cultivar of *Hydrangea* plant known by the varietal name 'Strared'. The new variety was discovered in 2014 in a planned breeding program in Harderwijk, The Netherlands. The purpose of the breeding program was to develop *Hydrangeas* with improved green-like flower colors and more vintage visual appearance. The new variety is the result of a cross between breeding selection Seedling 1012 (female parent, unpatented) and Seedling 08006-2 (male parent, unpatented). The compact nature of 'Strared' is similar to its female parent, but it differs from Seedling 1012 in flower color (red) and leaf sheen. The presence of green-colored flowers of 'Strared' is similar to its male parent, but it differs from Seedling 08006-2 in having darker colored leaves and an earlier flowering time. Further, when compared to *Hydrangea* variety named 'Stramini' (U.S. Plant Pat. No. 24,976), 'Stramini' exhibits predominantly green-colored flowers with some hot pink coloring present, while 'Strared' exhibits mostly deep red-colored flowers with some green coloring present. The new variety was first asexually reproduced in 2015 via propagation by stem cuttings in Harderwijk, The Netherlands. The new variety has been trial and field tested in Harderwijk, The Netherlands and has been found to retain its distinctive characteristics and remain true to type through successive propagations.

The following traits distinguish 'Strared' as a new and distinct cultivar from other Hydrangea varieties known to the breeder:

1. Deep red and green-colored flowers; and
2. Strong stems.

DESCRIPTION OF THE DRAWINGS

The accompanying photographic drawings illustrate the new variety taken at approximately 2 years of age, with the color being as nearly true as is possible with color illustrations of this type.

DESCRIPTION OF THE PLANT

Figure 1:
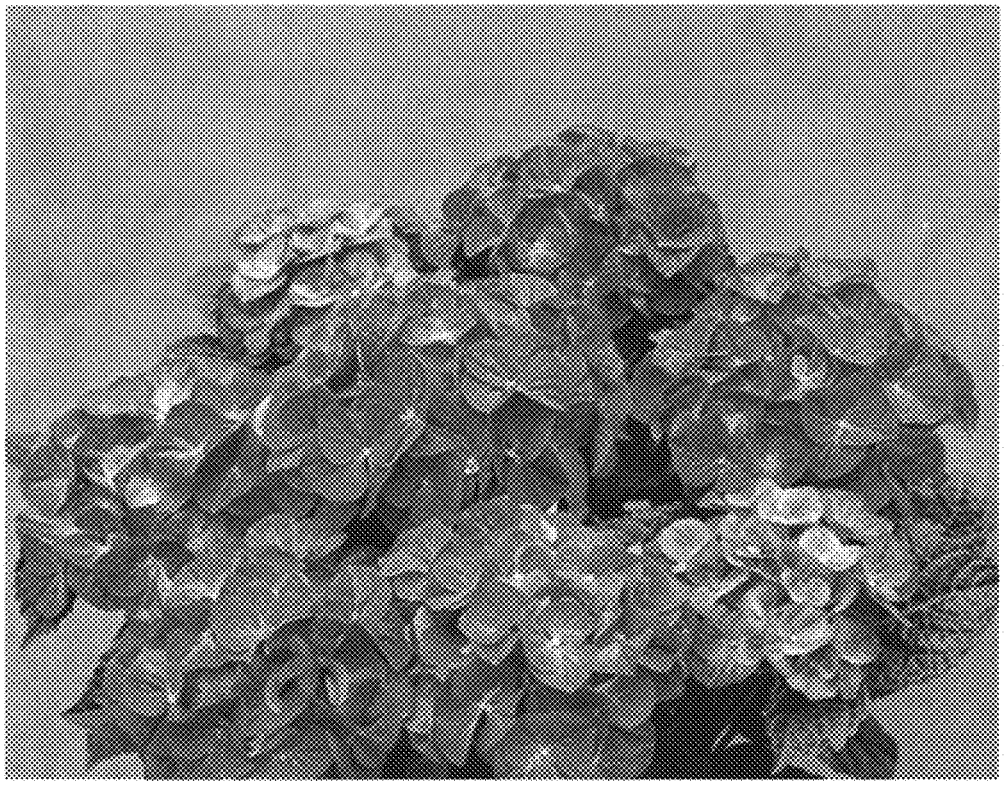
FIG. 1 is a photograph of a plant of the new variety.
Figure 2:
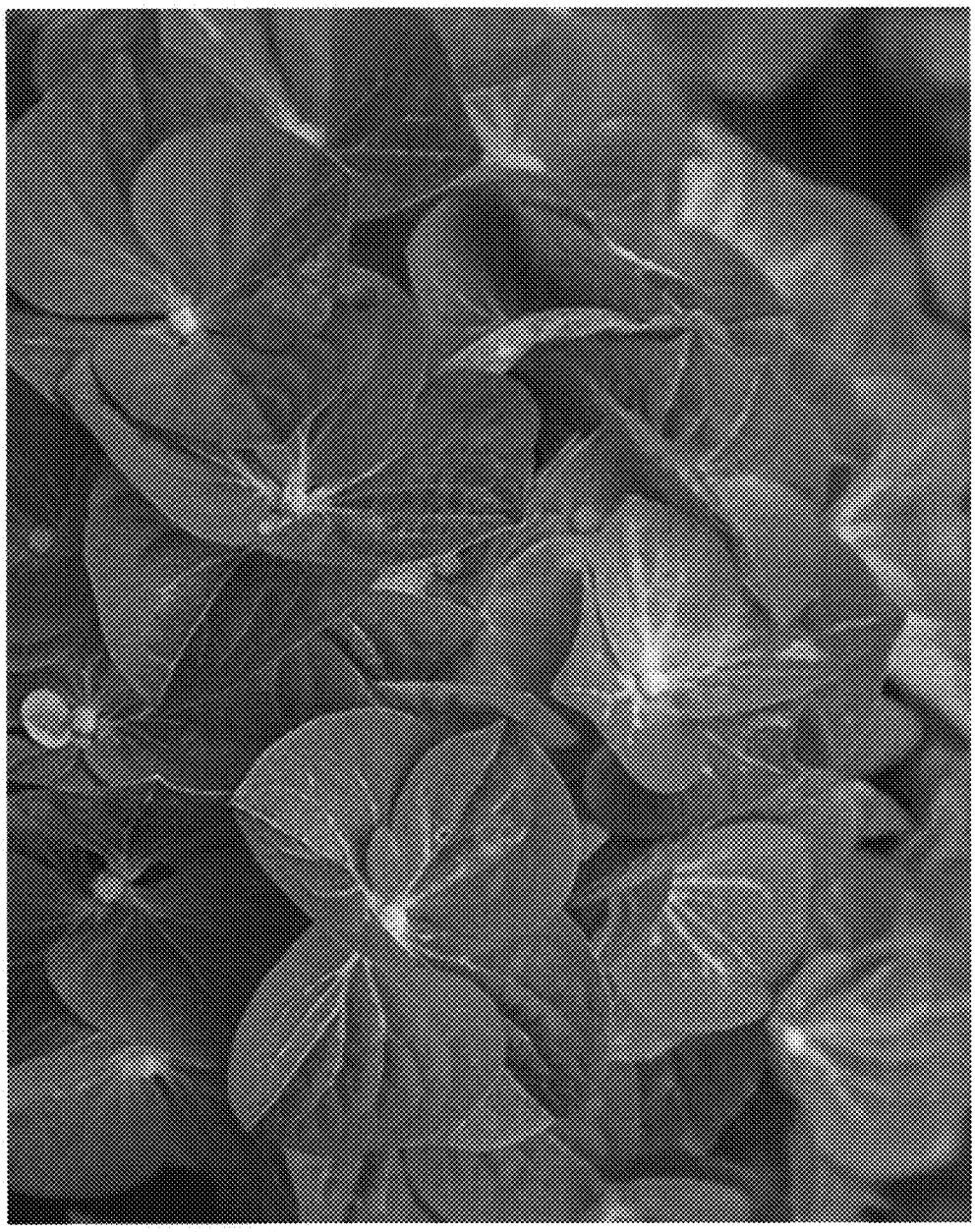
FIG. 2 is a close-up photograph of the flowers of the new variety.

The following detailed description sets forth characteristics of the new cultivar. The plants were grown in 15 cm pots, 8 per $m^2$, in ordinary potting soil with granulated fertilizers at a pH of 6.0. The plants were two years old when described. Measurements and color readings of the plants were taken in Harderwijk, The Netherlands under natural light. Color references are primarily to The HTML Color Chart.

Plant:

*Time to initiate roots.*—About 14 days at 22° C.
*Time to develop roots.*—About 18 days at 18-20° C.
*Rooting habit.*—Moderate.
*Time to produce a finished flowering plant from a rooted cutting.*—About 48 weeks in a 15 cm. container.
*Form.*—Mounded; non-climbing; upright.
*Height (from media surface to top of foliage).*—35-40 cm.
*Height (from media surface to top of flowers).* —40-45 cm.
*Plant diameter.*—35-40 cm.
*Vigor.*—Good.
*Strength.*—Good.
*Branching habit.*—Moderately-branched.
*Temperature tolerance.*—Heat tolerance to 30° C. and frost tolerance to 15° C.
*Trunk.*—Main trunk length: 8 cm. Diameter: 1 cm. Color: Green 6B 8E 23. Texture: Smooth. Pubescence: Absent. Internode length: 1.5-2 cm. Fasciation: None present. Lenticel color: Brown 5E 26 12.
*Lateral branches.*—Length: 25-30 cm. Diameter: 0.5 cm. Internode length: 6 cm. Texture: Shiny. Pubescence: Absent. Color: Green 7F FF 00.

*Foliage.*—Arrangement: Single. Stipules: None present. Size of leaf: Length: 12 cm. Width: 7-8 cm. Shape of leaf (generally): Young: Elliptic/obtuse. Mature: Elliptic/obtuse. Shape of apex: Lanceolate. Shape of base: Round. Texture: Smooth (both surfaces). Aspect: V-formed. Margin type: Serrate. Pubescence: None present. Lobing: Absent. Variegation: Absent. Color: Young leaves: Upper surface: Forest Green 22 8B 22. Lower surface: Forest Green 22 8B 22. Mature leaves: Upper surface: Dark Green 00 64 00. Lower surface: Dark Green 00 64 00. Petiole: Shape: Square. Length: 2 cm. Diameter: 0.5 cm. Color: Green 6B 8E 23. Veins: Type: Cross-venulate. Color: Upper surface: Olive 80 80 00. Lower surface: Olive 80 80 00.

Flower:

*Natural flowering season.*—May until October in Harderwijk, The Netherlands.

*Blooming habit.*—Continuous from late spring through summer with blooms lasting through fall.

*Bud* (*measurements made when cluster size was* 3 *cm*).—Shape of cluster: Round. Diameter of cluster: 3 cm. Number of buds per cluster: 40-50. Shape: Ball. Length: 0.3 cm. Width: 0.3 cm.

*Inflorescence.*—Shape: Round. Length: 16-20 cm. Diameter: 16-20 cm. Average number of flowers per inflorescence: 40. Typical number of inflorescences per plant: 6. Lastingness of an individual flower: 8 weeks. Lastingness of an inflorescence: 8 weeks. Conspicuousness of fertile flowers: Slightly inconspicuous. Flower type of a sterile flower: Single. Average calyx diameter of a sterile flower: 15 mm.

*Petaloids.*—Number per flower: 5. Color: Upper surface: Pink FF C0 CB. Lower surface: Pink FF C0 CB. Shape: Lanceolate and attenuate. Length: 0.3 cm. Width: 0.3 cm. Apex: Triangular. Base: Flat. Margin: Erect. Texture: Smooth (both surfaces). Tonality from a distance: Full.

*Petaloid sepals.*—Quantity: 5. Shape: Pointed. Apex: Pointed. Base: Round. Margin: Round. Length: 2 cm. Width: 3 cm. Color: Upper surface: Multicolored; Crimson DC 14 3C, Dark Red 8B 00 00, and Olive 80 80 00. Lower surface: Multicolored; Crimson DC 14 3C and Olive 80 80 00.

*Pedicels.*—Length: 2 cm. Diameter: 0.2 cm. Color: Multicolored; Crimson DC 14 3C and Olive 80 80 00.

*Peduncles.*—Length: 3-4 cm. Diameter: 0.3-0.4 cm. Texture: Smooth. Color: Olive 80 80 00.

*Stamens.*—Number per flower: 10. Filament: Length: 0.3 cm. Color: FA EB D7. Anthers: Shape: Elongated oval. Length: 0.2 cm. Color: Medium Purple 93 70 DB. Pollen: Color: Beige F5 F5 DC. Amount: Abundant.

*Pistils* (*fertile flowers*).—Number: 3. Length: 0.3 cm. Style: Length: 0.2 cm. Color: Light Pink FF B6 C1. Stigma: Shape: Long and oval. Color: FA EB D7. Size: 0.15 cm. Ovaries (superior): Length: 0.2 cm. Width: 0.2 cm. Color: Beige F5 F5 DC.

*Fragrance.*—None observed.

*Disease resistance.*—Tolerant to Botrytis.

*Temperature tolerance.*—Very good as long as direct sunlight is limited.

*Drought tolerance.*—Medium.

*Fruit.*—None observed.

We claim:

1. A new and distinct variety of *Hydrangea* plant, substantially as shown and described herein.

* * * * *